US005567361A

United States Patent [19]
Harper

[11] Patent Number: 5,567,361
[45] Date of Patent: Oct. 22, 1996

[54] FRAGRANCE ENHANCER APPARATUS

[76] Inventor: Edward C. Harper, 1429 Dewey Mimbs Rd., Dublin, Ga. 31027

[21] Appl. No.: 502,476

[22] Filed: Jul. 14, 1995

[51] Int. Cl.$^6$ ........................................................ B01F 3/04
[52] U.S. Cl. .................................... 261/26; 261/DIG. 65; 261/99; 422/124
[58] Field of Search ............................. 261/26, DIG. 65, 261/99; 422/124

[56] References Cited

U.S. PATENT DOCUMENTS

| | | | |
|---|---|---|---|
| 888,393 | 5/1908 | Dunning | 261/DIG. 65 |
| 1,614,817 | 1/1927 | Andrew | 261/DIG. 65 |
| 3,930,797 | 1/1976 | Gertz | 261/DIG. 65 |
| 3,990,848 | 11/1976 | Corris | 422/124 |
| 3,993,444 | 11/1976 | Brown | 422/124 |
| 4,078,891 | 3/1978 | Madjar | 261/DIG. 65 |
| 4,166,087 | 8/1979 | Cline et al. | 261/30 |
| 5,105,133 | 4/1992 | Yang | 422/124 |

FOREIGN PATENT DOCUMENTS 2222775  3/1990  United Kingdom ................... 422/124

Primary Examiner—Tim R. Miles

[57] ABSTRACT

A fragrance enhancer apparatus including a hollow container with a plurality of vent holes formed thereon and with the container having a size for holding a replaceable wick fragrance material therein; an electrically energizable fan disposed within the container for forcing air therefrom through the vent holes; an electrically energizable and user adjustable timer mechanism coupled to the container for allowing the fan to be electrically energized for a period of time; a power supply mechanism for supplying electrical energy for use; and a power switch mechanism coupled between the timer mechanism and power supply mechanism for selectively energizing and de-energizing the timer mechanism.

1 Claim, 4 Drawing Sheets

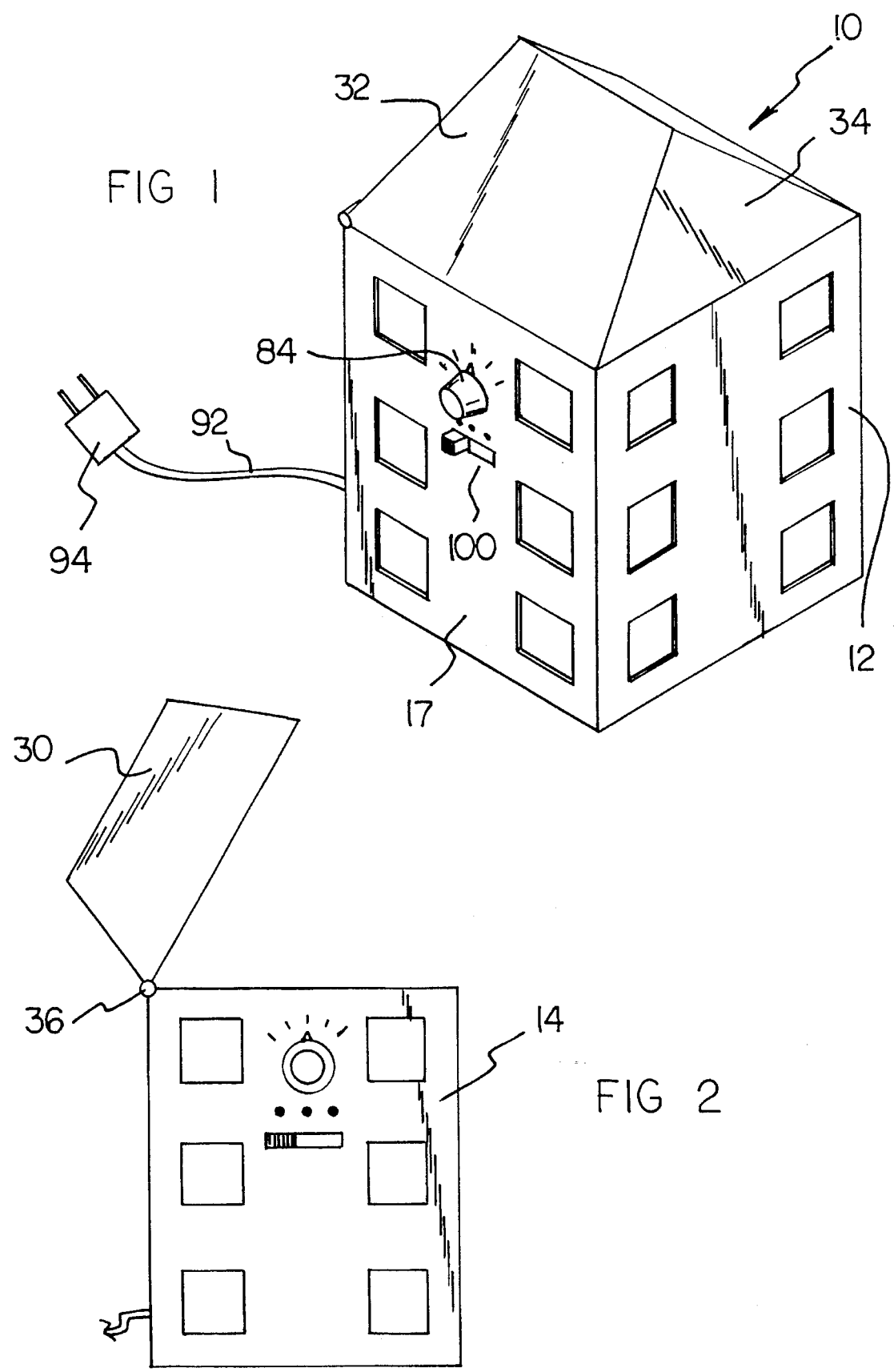

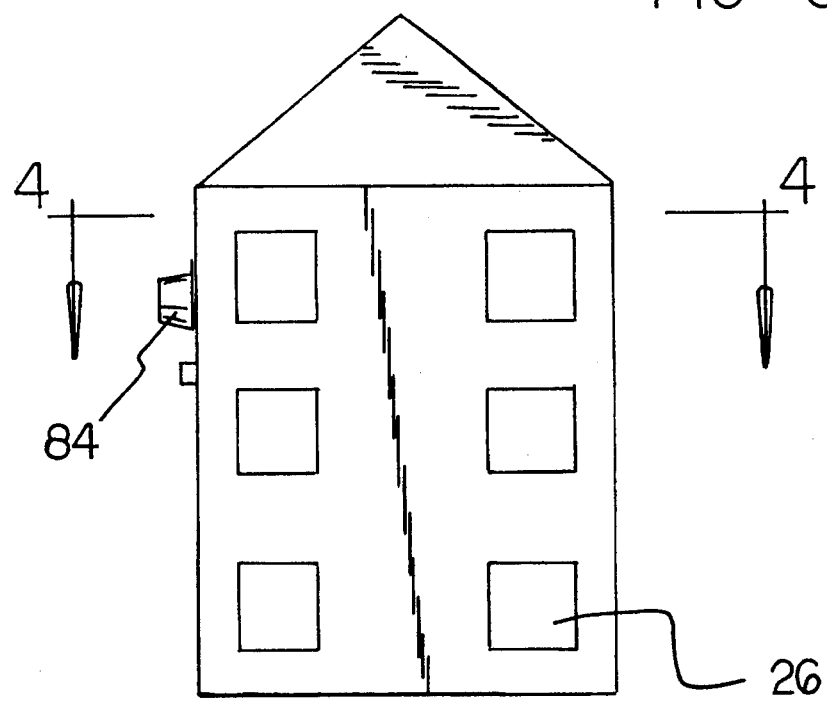
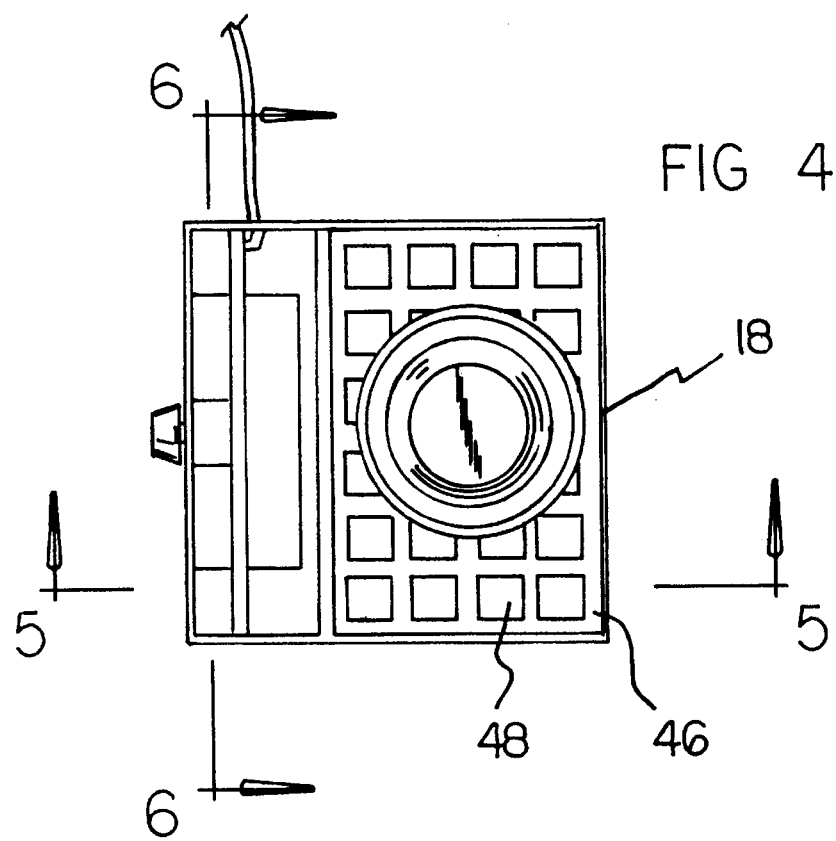

FRAGRANCE ENHANCER APPARATUS

BACKGROUND OF THE INVENTION

1. Field of the Invention

The present invention relates to a fragrance enhancer apparatus and more particularly pertains to maximizing the effectiveness of a wick air freshener by accumulating fragrance from the air freshener in an enclosed area and then expelling the fragrance with forced air with a fragrance enhancer apparatus.

2. Description of the Prior Art

The use of scenting apparatuses is known in the prior art. More specifically, scenting apparatuses heretofore devised and utilized for the purpose of freshening air are known to consist basically of familiar, expected and obvious structural configurations, notwithstanding the myriad of designs encompassed by the crowded prior art which have been developed for the fulfillment of countless objectives and requirements.

By way of example, U.S. Pat. Design No. 315,789 to Muderlak discloses an electrical air freshener. U.S. Pat. No. 4,035,451 to Tringali discloses a cartridge forming part of a system for inducing air flow past a product capable of being vaporized. U.S. Pat. No. 4,064,573 to Calderone discloses a cleanser/sanitizer and timed cycle deodorizing spray attachment for toilets. U.S. Pat. No. 4,111,655 to Quincey discloses electrically operated air fresheners. U.S. Pat. No. 5,186,869 to Stumpf et al. discloses an electronically controlled central air freshening system and method for using same.

While these devices fulfill their respective, particular objective and requirements, the aforementioned patents do not describe a fragrance enhancer apparatus that allows the effectiveness of a conventional wick type air freshener to be enhanced.

In this respect, the fragrance enhancer apparatus according to the present invention substantially departs from the conventional concepts and designs of the prior art, and in doing so provides an apparatus primarily developed for the purpose of maximizing the effectiveness of a wick air freshener by accumulating fragrance from the air freshener in an enclosed area and then expelling the fragrance with forced air.

Therefore, it can be appreciated that there exists a continuing need for new and improved fragrance enhancer apparatus which can be used for maximizing the effectiveness of a wick air freshener by accumulating fragrance from the air freshener in an enclosed area and then expelling the fragrance with forced air. In this regard, the present invention substantially fulfills this need.

SUMMARY OF THE INVENTION

In the view of the foregoing disadvantages inherent in the known types of scenting apparatuses now present in the prior art, the present invention provides an improved fragrance enhancer apparatus. As such, the general purpose of the present invention, which will be described subsequently in greater detail, is to provide a new and improved fragrance enhancer apparatus and method which has all the advantages of the prior art and none of the disadvantages.

To attain this, the present invention essentially comprises, in combination, a container. The container includes a box-shaped rigid body having a rectangular planar bottom wall with a rectangular planar front wall, a rectangular planar rear wall, and a pair of opposed rectangular planar side walls extended perpendicularly upwards from the bottom wall to define a hollow interior, a top edge, and a central opening for allowing access to the interior. Each wall of the container further has a plurality of rectangular-shaped vent holes disposed thereon. The container includes a rigid peaked roof formed of a pair of trapezoidal-shaped side faces with a pair of opposed triangular-shaped end faces extended therebetween and with the roof hingably coupled to the top edge of the body and positionable over the central opening thereof. The container includes a rigid perforated upstanding inner side wall coupled to the bottom wall and extended upwards therefrom to divide the interior into a first holding space and a second holding space. Lastly, the container includes a rigid perforated floor disposed within the second holding space and extended between the inner side wall and rear wall.

An electrically energizable fan is included and disposed within the first holding space for forcing air into the second holding space when electrically energized. An electrically energizable and user adjustable timer mechanism is included and disposed within the first holding space, extended through the face of the container, and coupled to the fan for allowing the fan to be electrically energized for a period of time. A power supply mechanism is included for converting electrical energy from an external power source to a form compatible for use by the timer mechanism. A power switch mechanism is included. The power switch mechanism is coupled between the timer mechanism and power supply mechanism and extended through the front wall of the container for selectively energizing and de-energizing the timer mechanism. Lastly, a replaceable wick air freshener material is provided and disposed upon the floor of the container. The wick air freshener material releases a fragrance within the container that is first accumulated and then expelled by forced air from the fan.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved fragrance enhancer apparatus which has all the advantages of the prior art scenting apparatuses and none of the disadvantages.

It is another object of the present invention to provide a new and improved fragrance enhancer apparatus which may be easily and efficiently manufactured and marketed.

It is a further object of the present invention to provide a new and improved fragrance enhancer apparatus which is of durable and reliable construction.

An even further object of the present invention is to provide a new and improved fragrance enhancer apparatus which is susceptible of a low cost of manufacture with regard to both materials and labor, and which accordingly is then susceptible of low prices of sale to the consuming public, thereby making such a fragrance enhancer apparatus economically available to the buying public.

Still yet another object of the present invention is to provide a new and improved fragrance enhancer apparatus which provides in the apparatuses and methods of the prior art some of the advantages thereof, while simultaneously overcoming some of the disadvantages normally associated therewith.

Even still another object of the present invention is to provide a new and improved fragrance enhancer apparatus for maximizing the effectiveness of a wick air freshener by accumulating fragrance from the air freshener in an enclosed area and then expelling the fragrance with forced air.

Lastly, it is an object of the present invention to provide a new and improved fragrance enhancer apparatus comprising a hollow container with a plurality of vent holes formed thereon and with the container having a size for holding a replaceable wick fragrance material therein; an electrically energizable fan disposed within the container for forcing air therefrom through the vent holes; electrically energizable and user adjustable timer means coupled to the container for allowing the fan to be electrically energized for a period of time; power supply means for supplying electrical energy for use; and power switch means coupled between the timer means and power supply means for selectively energizing and de-energizing the timer means.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of the preferred embodiment constructed in accordance with the principles of the present invention.

FIG. 2 is a side-elevational view of the preferred embodiment of the present invention with its roof in an open orientation.

FIG. 3 is yet another side-elevational view of the preferred embodiment of the present invention with its roof in a closed orientation.

FIG. 4 is a view of the present invention taken along the line 4—4 of FIG. 3.

The same reference numerals refer to the same parts through the various Figures.

DESCRIPTION OF THE PREFERRED EMBODIMENT

Figure 5:
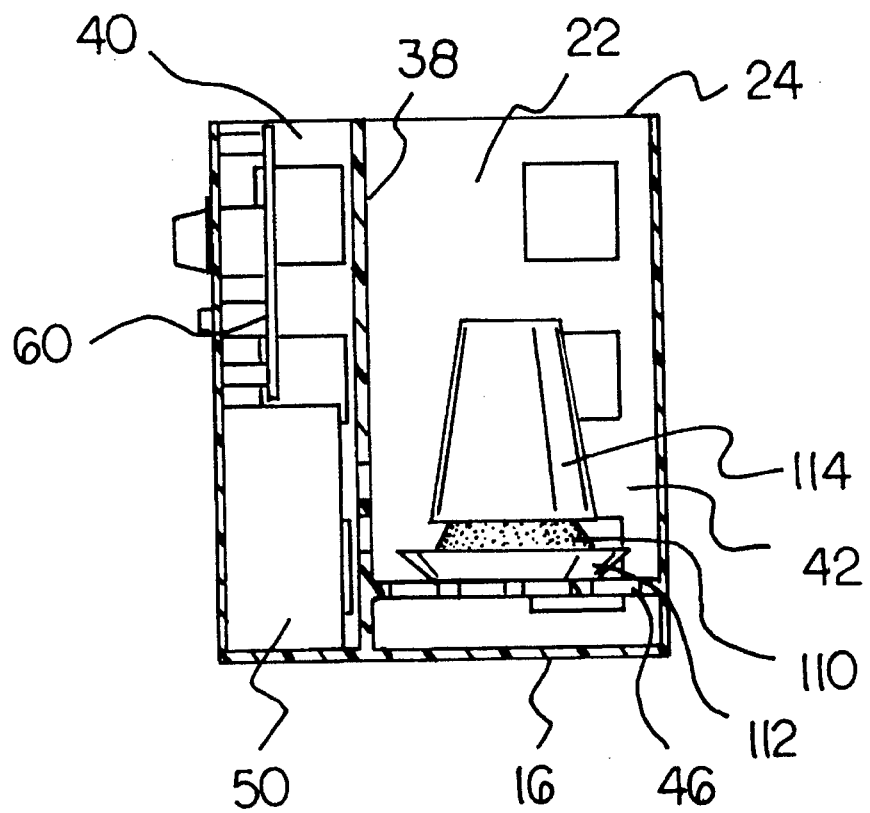
FIG. 5 is a cross-sectional view of the present invention taken along the line 5—5 of FIG. 4.
Figure 6:
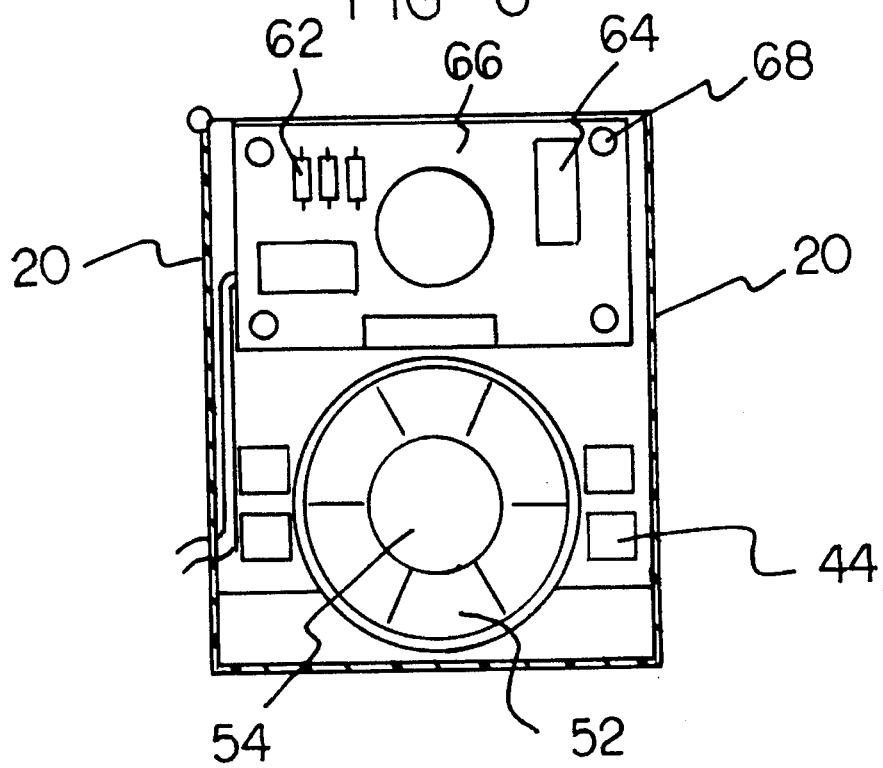
FIG. 6 is a cross-sectional view of the present invention taken along the line 6—6 of FIG. 4.

With reference now to the drawings, and in particular, to FIG. 1 thereof, the preferred embodiment of the new and improved fragrance enhancer apparatus embodying the principles and concepts of the present invention and generally designated by the reference number 10 will be described.

The preferred embodiment of the present invention comprises a plurality of components. In their broadest context, such components include a container, fan, timer mechanism, power supply mechanism, and power switch mechanism. Such components are individually configured and correlated with respect to each other to provide a structure that maximizes the effectiveness of a wick air freshener by accumulating fragrance from the air freshener in an enclosed area and then expelling the fragrance with forced air.

Specifically, the present invention includes a container 12 as shown in FIG. 1. The container is formed of a rigid impact-resistant plastic. The container includes a box-shaped body 14. The body has a rectangular planar bottom wall 16 with a rectangular planar front wall 17, a rectangular planar rear wall 18, and a pair of opposed rectangular side walls 20 extended perpendicularly upwards therefrom. The walls in combination define a hollow interior 22, a top edge 24, and a central opening for allowing access to the interior. Each wall further has a plurality of rectangular-shaped vent holes 26 disposed thereon. The vent holes place air exterior to the container in communication with air in the interior of the container. In the preferred embodiment, the front wall, the rear wall, and the side walls each have six vent holes disposed thereon arranged in a 2×3 matrix. Such matrix provides optimal ventilation.

Additionally, the housing includes a peaked roof 30. The peaked roof is formed of a pair of angularly positioned trapezoidal-shaped side faces 32 joined at an apex with a pair of opposed triangular-shaped end faces 34 extended therebetween. The roof is coupled to the top edge 24 of the body at one wall thereof with a hinge 36. The roof is positionable over the central opening of the container and upon its top edge. In the preferred embodiment, the container thus resembles a small house.

Disposed within the container is an upstanding planar rigid plastic inner side wall 38. The inner side wall is coupled to the bottom wall 16 and extended upwards therefrom and has an upper edge positioned flush with the top edge 24 of the body. The inner side wall divides the interior 22 into a first holding space 40 and a second holding space 42. The inner side wall also has a plurality of square perforations 44 formed thereon. The perforations allow communication between the first holding space and the second holding space.

A planar rigid plastic floor 46 is also provided and disposed within the second holding space 42. The floor is horizontally extended between and coupled to the inner side wall 38 and rear wall 18. A 6×9 matrix of rectangular perforations 48 are disposed upon the floor to essentially create a grate.

Disposed within the first holding space 40 is an electrically energizable fan 50. The fan is operable off of 12 volt DC electrical power and is used for forcing air exterior to the container into the second holding space 42 when the fan is electrically energized. The fan includes a plurality of radially extended blades 52 coupled to a central hub 54. Each blade is angularly offset from a vertical plane of rotation.

Figure 7:
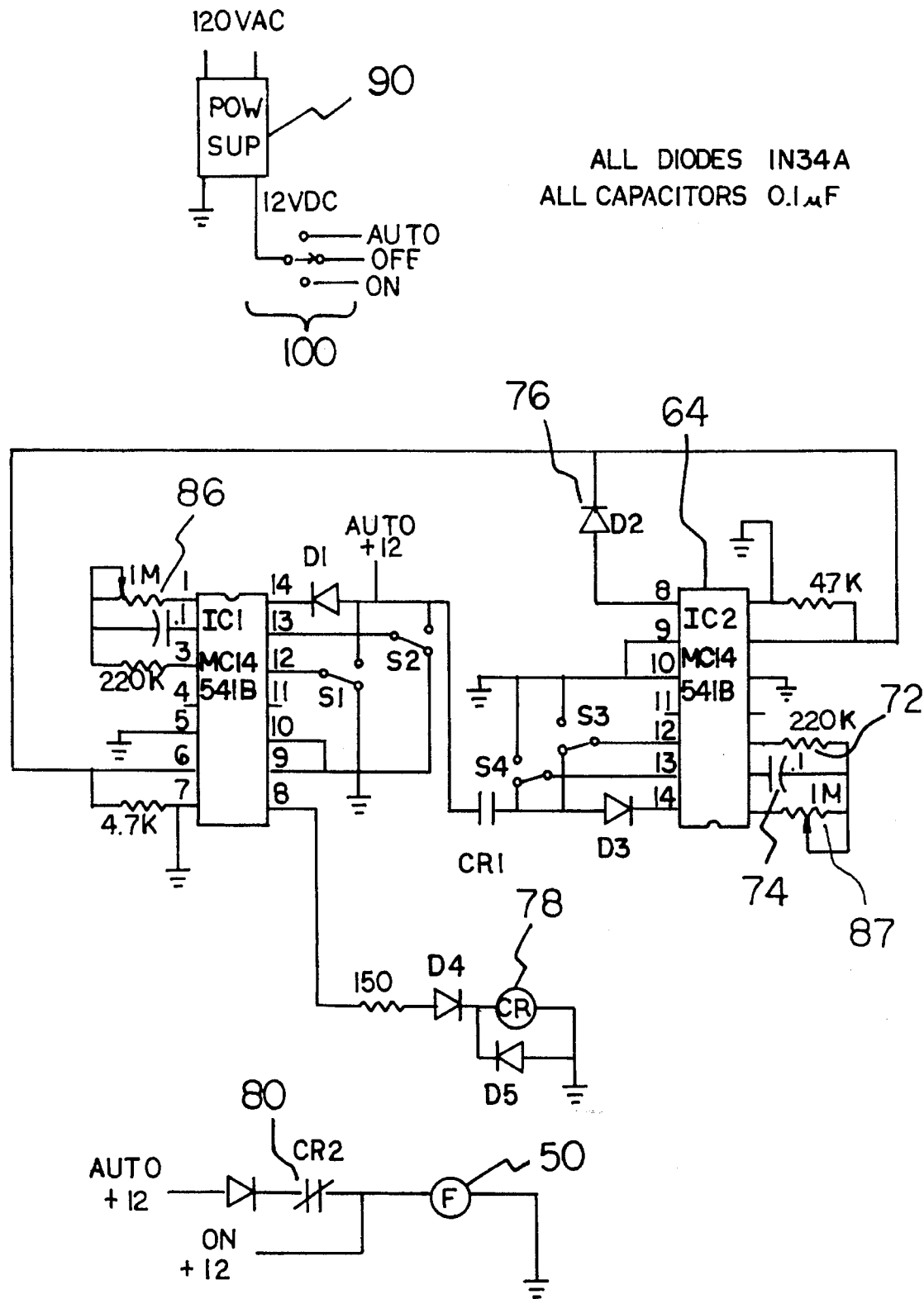
FIG. 7 is an electrical schematic diagram of the preferred embodiment of the present invention.

Disposed within the first holding space is an electrically energizable and user adjustable timer mechanism 60. The timer mechanism is coupled to the fan 50 for allowing the fan to be electrically energized for a period of time. The timer mechanism includes conventional commercially available electronic components 62 and integrated circuits 64 mounted on a printed circuit board 66. The printed circuit board is secured to the front wall 17 of the container with fasteners 68. As shown in FIG. 7, the timer mechanism uses two MC14541 programmable integrated circuits. IC1 controls the OFF delay time and IC2 controls the ON delay time. The ON delay time allows the fan to be activated for a period of time, and the off delay time allows the fan to be deactivated for a period of time. Provided below are the pinout tables for the MC14541 integrated circuit as used in this application:

TABLE 1

PIN AND ASSOCIATED FUNCTION

| PIN | FUNCTION |
| --- | --- |
| 1, 2, 3 | Sets the input frequency |
| 4 | Non-applicable |
| 5 | Ground |
| 6 | Reset |
| 7 | Ground |
| 8 | Output |
| 9 | Ground |
| 10 | Ground |
| 11 | Non-applicable |
| 12, 13 | Sets the count value as shown in the Table 2 below |
| 14 | 12 volts DC |

TABLE 2

COUNT (TIME PERIOD) FOR PINS 12 and 13

| PIN 12 | PIN 13 | COUNT |
| --- | --- | --- |
| 1 | 0 | 256 |
| 0 | 1 | 1024 |
| 0 | 0 | 8192 |
| 1 | 1 | 65536 |

The integrated circuits IC1 and IC2 are interconnected with an activation network formed by resistors 72, capacitors 74, and diodes 76. A 70 ohm control relay 78 is used to supply power to the fan and IC2. The output at pin 8 on IC1 picks up on or energizes relay 78. Secondary relay 80 also controls switching action of the fan. The output at pin 8 on IC2 resets IC1 and stops the fan. This cycle is repeated as long as power is applied to the circuit. All diodes are commercially available and of the 1N34A type. All capacitors have a value of 0.1 microfarads. Resistor values are as shown in FIG. 7. Switches S1 through S4 are used for setting a count value or time period for controlling the ON delay time and the OFF delay time. Switching action through switches S1 through S4 is realized through the use of a dial 84 extended through the front wall 17 of the container. Potentiometer 86 is connected to IC1, and potentiometer 87 is connected to IC2. Both potentiometers 86, 87 can be user adjustable to adjust cycling times linearly from zero to maximum seconds, minutes or hours.

A power supply mechanism 90 is used for converting 120 VAC electrical energy from an external power source to a 12 VDC form that is compatible for use by the timer mechanism 60. The power supply mechanism is conventional in design. An electrically conductive cord 92 is extended from the power supply mechanism 90 and through the container and terminated at a pronged plug 94. The plug is securable within an external power source such as a conventional household electrical socket for receiving electrical energy for use. Coupled between the timer mechanism 60 and power supply mechanism 90 is a power switch 100. The power switch is extended through the front wall 17 of the container. The power switch has a first position for energizing the timer circuitry, a second position for de-energizing the timer circuitry, and a third position for allowing the timer mechanism to operate in an automatic-type mode. In the automatic-type mode, the timer mechanism continually cycles through the ON delay times and the OFF delay times in a sequential fashion.

Additionally, a replaceable wick air freshener material 110 is disposed upon the floor 46 of the container. The wick air freshener material releases a fragrance within the container. This fragrance is first accumulated within the interior of the container and then forcibly expelled by air from the fan for a given period of time. The wick air freshener material is disposed within a housing with a bottom plate 112 and an openable cup 114. The wick air freshener material and housing are conventional in design and commercially available. Other similar freshener materials such as a potpourri can also be used.

The present invention maximizes the effectiveness of common household air fresheners, particularly the wick type. Common wick-type air fresheners are generally placed on an object in a corner, on a shelf, or out of view, thereby losing their freshening effectiveness due to lack of ventilation applied thereon. Common wick-type air fresheners are most effective when they are put into use for an extended period of time in a ventilated area. However, after only a few hours, they lose their maximum effectiveness and the amount of scent given off continues to degrade throughout the rest of the life of the air freshener. The present invention greatly improves the effectiveness of air fresheners by accumulating the fragrance in a decorative container and then expelling the accumulated fragrance periodically through the use of forced air. This forced air pushes the fragrance out into the room, thereby maximizing its freshening capability. The present invention also extends the life of common wick-type air freshener by controlling the air movement around it. Timing cycles of the present invention are accomplished through the use of a programmable timer mechanism that is programmed by the use of switches. The position of each switch determines the count value for ON and OFF delay time periods. The present invention can also be switched on for continuous operation when extra freshness is needed within a room. The housing of the present invention is about 5 inches wide and 8 inches tall and can be manufactured in materials such as ceramic or plastic. The present invention helps to maintain a consistent level of scent throughout a house or apartment. The fan also helps the fragrance from a freshener spread further and faster through a house or apartment. The present invention can be made in a variety of decorative shapes.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by LETTERS PATENT of the United States is as follows:

1. A fragrance enhancer apparatus for maximizing the effectiveness of a wick air freshener by accumulating fragrance from the air freshener in an enclosed area and then expelling the fragrance with forced air comprising, in combination:

a container further comprising:
      a box-shaped rigid body having a rectangular planar bottom wall with a rectangular planar front wall, a rectangular planar rear wall, and a pair of opposed rectangular planar side walls extended perpendicularly upwards from the bottom wall to define a hollow interior, a top edge, and a central opening for allowing access to the interior, each wall further having a plurality of rectangular-shaped vent holes disposed thereon;
      a rigid peaked roof formed of a pair of trapezoidal-shaped side faces with a pair of opposed triangular-shaped end faces extended therebetween and with the roof hingably coupled to the top edge of the body and positionable over the central opening thereof;
      a rigid perforated upstanding inner side wall coupled to the bottom wall and extended upwards therefrom to divide the interior into a first holding space and a second holding space; and
      a rigid perforated floor disposed within the second holding space and extended between the inner side wall and rear wall;
   an electrically energizable fan disposed within the first holding space for forcing air into the second holding space when electrically energized;
   electrically energizable and user adjustable timer means disposed within the first holding space, extended through the face of the container, and coupled to the fan for allowing the fan to be electrically energized for a period of time;
   power supply means for converting electrical energy from an external power source to a form compatible for use by the timer means;
   power switch means coupled between the timer means and power supply means and extended through the front wall of the container for selectively energizing and de-energizing the timer means; and
   a replaceable wick air freshener material disposed upon the floor of the container and with the material releasing a fragrance within the container that is first accumulated and then expelled by forced air from the fan.

* * * * *